(12) United States Patent
Hell

(10) Patent No.: US 6,909,017 B2
(45) Date of Patent: Jun. 21, 2005

(54) METHOD FOR ISOLATING AND PURIFYING (1RS,2RS)-2-[(DIMETHYLAMINO)METHYL]-1-(3-METHOXYPHENYL)CYCLOHEXANOL

(75) Inventor: Wolfgang Hell, Aachen (DE)

(73) Assignee: Grunenthal GmbH, Aachen (DE)

( * ) Notice: Subject to any disclaimer, the term of this patent is extended or adjusted under 35 U.S.C. 154(b) by 20 days.

(21) Appl. No.: 10/638,703

(22) Filed: Aug. 11, 2003

(65) Prior Publication Data

US 2004/0225154 A1 Nov. 11, 2004

Related U.S. Application Data

(63) Continuation of application No. PCT/EP02/01764, filed on Feb. 20, 2002.

(30) Foreign Application Priority Data

Feb. 21, 2001 (DE) .......................... 101 08 308

(51) Int. Cl.$^7$ ............................ C07C 213/10
(52) U.S. Cl. .................. 564/425; 564/339; 548/211
(58) Field of Search ................. 564/339, 425; 548/211

(56) References Cited

U.S. PATENT DOCUMENTS 3,652,589 A    3/1972  Flick et al. ............... 260/326.5
5,672,755 A  * 9/1997  Lerman et al. ............. 564/425
5,877,351 A    3/1999  Anderson .................. 564/425

FOREIGN PATENT DOCUMENTS

DE        19940740 A1       3/2001
WO        WO 99/61405       12/1999
WO        WO 00/78705 A1    12/2000

OTHER PUBLICATIONS

"Solvatochromic Dyes As Solvent Polarity Indicators", Reichardt, Chem. Rev. 1994, 94, pp. 2319–2358.

"Determination Of New And Corrections of Old $E_T(30)$ Values As Empirical Measures Of Solvent Polarity For 40 Organic Solvents", Reichardt et al., Liebigs Ann., 1995, pp. 1579–1582.

R. Eberhardt et al., "Determination of ET(30) Values of Supercritical Carbon Dioxide at Various Pressures and Temperatures" 1997, Germany, pp. 1195–1199.

* cited by examiner

Primary Examiner—Brian Davis
(74) Attorney, Agent, or Firm—Perman & Green, LLP.

(57) ABSTRACT

The invention relates to a method for isolating and purifying (1RS,2RS)-2-[(dimethylamino)methyl]-1-(3-methoxyphenyl)-cyclohexanol as a saccharinate from a mixture of the diastereomers (1SR,2)RS-2-[(dimethylamino)methyl]-1-(3-methoxyphenyl)-cyclohexanol and (1SR-2RS)-2-[(dimethylamino)methyl]-1-(3-methoxyphenyl)-cyclohexanol and optionally impurities.

28 Claims, No Drawings

METHOD FOR ISOLATING AND PURIFYING (1RS,2RS)-2-[(DIMETHYLAMINO)METHYL]-1-(3-METHOXYPHENYL)CYCLOHEXANOL

This application is a continuation of International Application Number PCT/EP02/01764 filed 20 Feb. 2002, status pending.

The present invention relates to a process for isolating and purifying (1RS,2RS)-2-[(dimethylamino)methyl]-1-(3-methoxyphenyl)cyclohexanol as the saccharinate from a mixture consisting of the diastereomers (1RS,2RS)-2-[(dimethylamino)methyl]-1-(3-methoxyphenyl)cyclohexanol and (1SR,2RS)-2-[(dimethylamino)methyl]-1-(3-methoxyphenyl)cyclohexanol and also in some cases impurities.

The active pharmaceutical ingredients (1RS,2RS)-2-[(dimethylamino)methyl]-1-(3-methoxyphenyl)cyclohexanol which is also obtainable on the market under the name Tramadol is frequently used in the form of its hydrochloride as an analgesic. One typical way of preparing this active ingredient is via a Grignard reaction to obtain the (1RS,2RS)-diastereomer in a mixture with the corresponding (1SR,2RS)-diastereomer, from which it has to be removed before formulation to give a medicament.

For the removal of the (1RS,2RS)-diastereomer from the corresponding (1SR,2RS)-diastereomer, various processes are known. They are based, inter alia, on the reaction of the (1RS,2RS)/(1SR,2RS)-diastereomer mixture with mineral acids and a subsequent fractional crystallization from organic solvents. A disadvantage of these processes is that several fractions are obtained in each case, each of which has to be worked up separately, thus reducing the economic viability of this process. Further, the use of concentrated mineral acids can lead to the occurrence of undesired decomposition products which complicate the purification of the (1RS,2RS)-diastereomer and reduce its yield. In addition, the existing processes can generally only achieve a removal of the (1RS,2RS)-diastereomer when the proportion of this diastereomer in the diastereomer mixture to be separated is about 75% by weight or more.

U.S. Pat. No. 5,877,351 describes a process for isolating and purifying the (1RS,2RS)-diastereomer from a reaction mixture which, in addition to the (1RS,2RS)/(1SR,2RS)-diastereomer mixture, also comprises impurities from the preceding Grignard reaction. In this process, removal of the (1RS,2RS)-diastereomer is achieved in the form of the corresponding hydrobromide by adding an aqueous solution of hydrogen bromide to the reaction mixture. A disadvantage of this process is that the resulting hydrobromide has to be converted to the corresponding hydrochloride salt before formulation to the medicament.

It was therefore an object of the present invention to provide a process for isolating and purifying (1RS,2RS)-2-[(dimethylamino)methyl]-1-(3-methoxy-phenyl)cyclohexanol, which provides this active ingredient not only in high purity and very good yields but also as a compound which can be used directly to produce a medicament.

According to the invention, this object is achieved by a process for isolating and purifying (1RS,2RS)-2-[(dimethylamino)methyl]-1-(3-methoxyphenyl)cyclohexanol as the saccharinate from a mixture consisting of the diastereomers (1RS,2RS)-2-[(dimethylamino)methyl]-1-(3-methoxyphenyl)cyclohexanol and (1SR,2RS)-2-[(dimethyl-amino)methyl]-1-(3-methoxyphenyl)cyclohexanol and also in some cases impurities, by reacting this mixture with saccharin in a liquid reaction medium having a polarity of at least 38 kcal/mol, removing the thus-obtained crystalline precipitate of the saccharinate of the (1RS,2RS)-2-[(dimethylamino)methyl]-1-(3-methoxyphenyl)-cyclohexanol diastereomer from the mother liquor, optionally washing at least once and/or optionally recrystallizing and subsequently drying at least once.

For the purposes of the present invention, polarity is the empirically determined solvent polarity $E_T(30)$ which is determined with the aid of the negatively solvatochromic pyridinium N-phenoxide betaine dye of the formula I below by measuring the longest wavelength absorption band in the visible/near infrared (Vis/NIR) region.

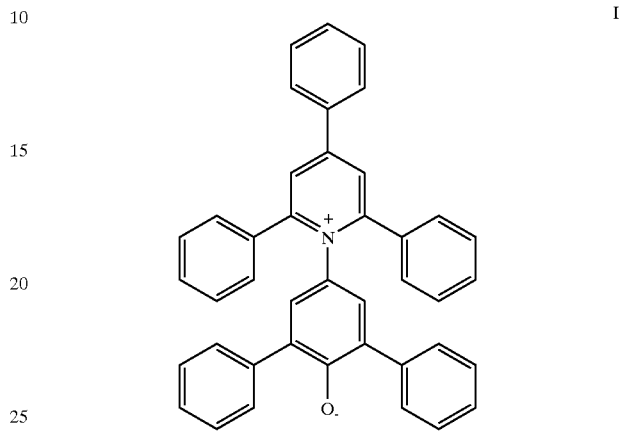

I

The methods for determining these $E_T(30)$ values and also the corresponding values for a multitude of reaction media are described, for example, in C. Reichardt, Chem. Rev. 1994, 94, pages 2319–2358, C. Reichardt and G. Schäfer, Liebigs Ann., 1995, pages 1579–1582 and in R. Eberhardt et al., 1997, Liebigs Ann./Recueil, pages 1195–1199. These literature descriptions are hereby introduced by way of reference and are therefore included in the disclosure-content.

In a preferred embodiment of the process according to the invention, a reaction medium having a polarity of at least 45 kcal/mol, more preferably at least 55 kcal/mol, is used.

For the purpose of the present invention, the (1RS,2RS)-2[(dimethylamino)methyl]-1-(3-methoxyphenyl)-cyclohexanol diastereomer is the racemate of the compounds of the formulae IIa and IIb illustrated below:

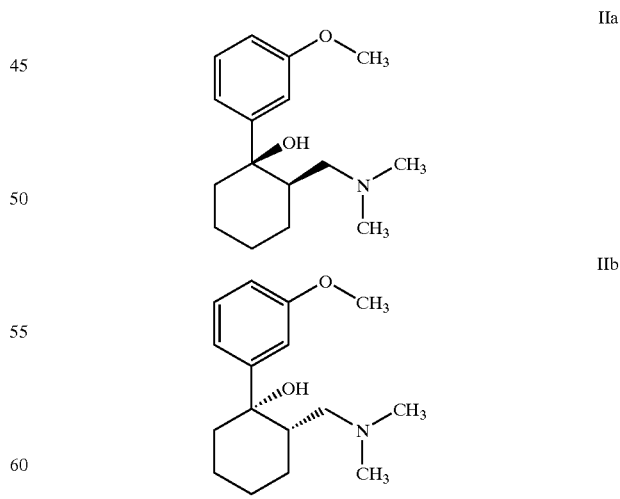

The enantiomer of the formula IIa is (1R,2R)-2[(dimethylamino)methyl]-1-(3-methoxyphenyl)cyclohexanol, and the enantiomer of the formula IIb (1S,2S)-2-[(dimethylamino)methyl]-1-(3-methoxyphenyl)cyclohexanol.

For the purposes of the present invention, the (1SR,2RS)-2-[(dimethylamino)methyl]-1-(3-methoxy-phenyl)cyclohexanol diastereomer is the racemate of the compounds of the formulae IIIa and IIIb illustrated below:

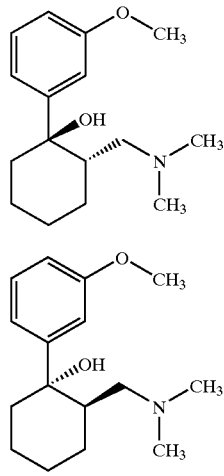

IIIa

IIIb

In a preferred embodiment of the process according to the invention, the (1RS,2RS)/(1SR,2RS)-diastereomer mixture comprises at least 50% by weight, preferably at least 60% by weight, of the (1RS,2RS)-2-[(dimethyl-amino)methyl]-1-(3-methoxyphenyl)cyclohexanol diastereomer.

In a preferred embodiment of the process according to the invention, the reaction medium which is liquid at 20° C. and atmospheric pressure, apart from water, is a low molecular weight organic compound having the specified polarity, such as an aliphatic alcohol, preferably of $C_1$–$C_4$, an aliphatic ketone, preferably of $C_3$–$C_7$, an aliphatic ester, preferably of $C_2$–$C_6$, an aliphatic and/or aromatic ester, preferably of $C_7$–$C_{12}$, an aliphatic or aromatic ether, preferably an aliphatic ether of $C_4$–$C_6$, a haloalkane, preferably of $C_1$–$C_2$, an aliphatic or aromatic nitrile, a polyol, preferably a polyol of $C_2$–$C_{10}$, or a mixture of at least two of these aforementioned compounds. The liquid reaction medium used in the process according to the invention is more preferably water, methanol, ethanol, n-propanol, isopropanol, n-butanol, isobutanol, ethyl acetate, n-butyl acetate, methyl formate, methyl ethyl ketone, diisopropyl ether, anisole, ethylene glycol, propylene glycol, acetone or a mixture of at least two of these aforementioned compounds. Very particularly preferred mixtures of water and an organic compound are mixtures of water and ethanol or of water and acetone.

When a mixture of water and one of the aforementioned organic compounds is used in the process according to the invention, this may preferably comprise from 60 to 95% by weight of the organic compound and from 5 to 40% by weight of water, more preferably from 70 to 90% by weight of the organic compound and from 10 to 30% by weight of water, most preferably from 75 to 85% by weight of the organic compound and from 15 to 25% by weight of water, based in each case on the total amount of the reaction medium.

In a further preferred embodiment of the process according to the invention, the mixture of the (1RS,2RS)/(1SR,2RS)-diastereomers and in some cases impurities is cooled during and/or immediately after the reaction with the saccharin. The temperature to be attained to obtain a maximum yield of the desired (1RS,2RS)-diastereomer depends, for example, on the reaction medium used and can be determined by those skilled in the art by simple preliminary experiments. Preference is given to cooling to a temperature in the range from 2 to 15° C., more preferably in the range from 5 to 10° C., and the reaction medium should remain solid at these temperatures.

Preference is likewise given to stirring the reaction mixture before removing the crystalline precipitate. The time for which the reaction mixture has to be stirred in order to obtain the maximum yield of the desired (1RS,2RS)-diastereomer depends, for example, on the reaction medium used and on the temperature, and can be determined by those skilled in the art by simple preliminary experiments. Preference is given to stirring the reaction mixture for from 5 to 25 hours, more preferably from 10 to 20 hours. Useful stirring apparatus for this purpose is the customary stirring apparatus known to those skilled in the art, for example an anchor stirrer.

The crystalline precipitate can be removed from the mother liquor by customary methods known to those skilled in the art. Preference is given to removing the crystalline precipitate by centrifugation, suction filtration, decanting or a combination of at least two of these aforementioned methods.

In some cases, it may be advantageous to wash the removed crystalline precipitate once or more, in order to further improve the purity of the (1RS,2RS)-2-[(dimethylamino)methyl]-1-(3-methoxyphenyl)cyclohexanol saccharinate.

The crystalline precipitate is preferably washed using the reaction medium in which the reaction with the saccharin has also been carried out.

Preference is given to cooling the reaction medium used to wash the precipitate, in order to prevent the crystalline precipitate from partly or completely dissolving therein. Preference is given to cooling the reaction medium to a temperature of from 2 to 15° C., more preferably from 5 to 10° C.

For further improvement of the purity of the (1RS,2RS)-diastereomer, it may also be advantageous to recrystallize the crystalline precipitate of the (1RS,2RS)-2-[(dimethylamino)methyl]-1-(3-methoxyphenyl)-cyclohexanol saccharinate once or more than once, or to stir it in a suitable medium. This recrystallization can be effected by customary methods known to those skilled in the art. Preference is given to recrystallizing the crystalline precipitate using the reaction medium in which the reaction with the saccharinate has been carried out.

The crystalline precipitate obtained after the reaction with saccharin or the washed and/or recrystallized precipitate can be dried by customary methods known to those skilled in the art. Preference is given to drying the crystalline precipitate in the course of or immediately after the removal of the mother liquor by suction filtration under air and/or drying in a drying cabinet, optionally with the application of a vacuum. When the precipitate is dried in a drying cabinet, the preferred temperature is from 35 to 45° C.

In a further preferred embodiment of the process according to the invention, the (1RS,2RS)/(1SR,2RS)-diastereomer mixture to be separated is reacted with the saccharin directly after the Grignard reaction to prepare the mixture, i.e. without any purification. The impurities are then by-products which stem from this Grignard reaction. The Grignard reaction and also possible by-products which occur are described, for example, in U.S. Pat. No. 5,877,351. The corresponding description therefrom is hereby introduced by way of reference and therefore forms part of the disclosure-content.

However, the (1RS,2RS)/(1SR,2RS)-diastereomer mixture may also have been freed of impurities before the reaction with the saccharin, for example by distillation under reduced pressure, as described, for example, in U.S. Pat. Nos. 5,877,351 or 3,652,589. The corresponding descriptions therefrom are hereby introduced by way of reference and thus form part of the disclosure-content.

The Grignard reaction for preparing the diastereomer mixtures may also be carried out in the presence of an additive, for example in the presence of an amine or of an ether, in order to achieve an improved (1RS,2RS)/(1SR,2RS)-diastereomer ratio, as described, for example, in WO 99/61405. This corresponding description therefrom is hereby introduced by way of reference and thus forms part of the disclosure-content.

The (1RS,2RS)-2-[(dimethylamino)methyl]-1-(3-methoxyphenyl)cyclohexanol saccharinate obtained by the process according to the invention is suitable directly for formulating a medicament. However, if necessary, the (1RS,2RS)-2-[(dimethylamino)methyl]-1-(3-methoxyphenyl) cyclohexanol active ingredient can also be obtained as the free base from the saccharinate.

In a further preferred embodiment of the process according to the invention, the (1RS,2RS)-2-[(dimethylamino) methyl]-1-(3-methoxyphenyl)cyclohexanol saccharinate is therefore released by reaction with a suitable base, for example sodium hydroxide, in a suitable organic solvent or solvent mixture, for example tetrahydrofuran or toluene. The base is added thereto in an equimolar amount or in excess, based on the (1RS,2RS)-2-[(dimethylamino)methyl]-1-(3-methoxyphenyl)cyclohexanol saccharinate. The free base of the (1RS,2RS)-diastereomer obtained in this way can be purified and isolated by customary methods known to those skilled in the art.

The free base of the (1RS,2RS)-diastereomer can be converted to the corresponding active ingredient salt by the reaction with corresponding acids by customary methods known to those skilled in the art. (1RS,2RS)-2-[(dimethylamino)methyl]-1-(3-methoxyphenyl) cyclohexanol can be converted to the corresponding hydrochloride salt, for example, by reaction with an aqueous solution of hydrogen chloride.

The process according to the invention has the advantage that the (1RS,2RS)-2-[(dimethylamino)methyl]-1-(3-methoxyphenyl)cyclohexanol active ingredient is obtained in very good yields and with a very high purity. Another advantage is that the active ingredient, after isolation and purification, is in the form of a corresponding saccharinate which is suitable directly for the formulation of a medicament and does not have to be converted by further process steps to another physiologically active salt, for example the corresponding hydrochloride.

The purity of the (1RS,2RS)-diastereomer or of a corresponding salt, i.e. the ratio of the (1RS,2RS)/(1SR,2RS)-diastereomer in the product obtained by the process according to the invention can be determined by customary methods known to those skilled in the art. Preference is given to determining the ratio of the diastereomers by means of HPLC on a V2A steel column (length 12.5 cm, diameter 3.0 mm) and of a Nucleosil 100-5μ C8 HD separating phase against a suitable standard, using a flow rate of 0.7 ml/min and a temperature of 25° C. The detection is at a wavelength of 270 nm.

The invention is illustrated hereinbelow with the aid of examples. These illustrations are merely by way of example and do not limit the general inventive concept.

EXAMPLES

In the inventive examples 1 to 5, a mixture is used which consists of (1RS,2RS)-2-[(dimethylamino)methyl]-1-(3-methoxyphenyl)cyclohexanol and (1SR,2RS)-2-[(dimethylamino)methyl]-1-(3-methoxyphenyl) cyclohexanol and further impurities and has been obtained from the Grignard reaction according to U.S. Pat. No. 3,652,589. The corresponding literature description therefrom is hereby introduced by way of reference and thus forms part of the disclosure-content. The mixture of the diastereomers and the impurities obtained in this way was used in examples 1 to 5 directly after the Grignard reaction, i.e. without any further purification.

Example 1

In a 10 liter jacketed reaction apparatus equipped with electric anchor stirrer, reflux condenser, thermometer and cooling/heating unit (from Huber, Unistat 161 W), 1.5 kg of the mixture obtained by the above-specified Grignard reaction were dissolved at a temperature of 20° C. in 5.0 liters of ethanol having a polarity of 51.9 kcal/mol. 1.04 kg of saccharin were added to this solution. Subsequently, this reaction mixture was cooled to a temperature of 8° C. and stirred at this temperature for a further 16 hours. This resulted in the formation of a crystalline precipitate of (1RS,2RS)-2-[(dimethylamino)methyl]-1-(3-methoxyphenyl)cyclohexanol saccharinate which was removed from the mother liquor by suction filtration under reduced pressure using a G3 frit. Subsequently, the precipitate was twice washed with 2.0 liters of ethanol each time which had been cooled beforehand to a temperature of 8° C., and then dried in a vacuum drying cabinet at a temperature of 40° C. and a pressure of 20 mbar for 16 hours. The yield of the product obtained in this way was 1.90 kg (corresponding to 75% of the theoretically calculated value) having a content of (1RS,2RS)-2-[(dimethylamino)methyl]-1-(3-methoxyphenyl)cyclohexanol saccharinate of >95% by weight.

Example 2

In a 20 liter jacketed reaction apparatus equipped with electric anchor stirrer, reflux condenser, thermometer and cooling/heating unit (from Huber, Unistat 161 W), 1.5 kg of the mixture obtained by the above-specified Grignard reaction were dissolved at a temperature of 20° C. in 12.5 liters of ethyl acetate having a polarity of 38.1 kcal/mol. 1.04 kg of saccharin were added to this solution. Subsequently, this reaction mixture was cooled to a temperature of 8° C. and stirred at this temperature for a further 16 hours. This resulted in the formation of a crystalline precipitate of (1RS,2RS)-2-[(dimethylamino)methyl]-1-(3-methoxyphenyl)-cyclohexanol saccharinate which was removed from the mother liquor by suction filtration under reduced pressure using a G3 frit. The crystalline precipitate was twice washed with 2.0 liters of ethyl acetate each time which had been cooled beforehand to a temperature of 8° C., and then dried in a vacuum drying cabinet at a temperature of 40° C. and a pressure of 20 mbar for 16 hours. The yield of the product obtained in this way was 2.16 kg (corresponding to 85% of the theoretically calculated value) having a content of (1RS,2RS)-2-[(dimethylamino)methyl]-1-(3-methoxyphenyl)cyclohexanol saccharinate of >92% by weight.

Example 3

In a 10 liter jacketed reaction apparatus equipped with electric anchor stirrer, reflux condenser, thermometer and cooling/heating unit (from Huber, Unistat 161 W), 1.5 kg of the mixture obtained by the above-specified Grignard reaction were dissolved at a temperature of 20° C. in 4.0 liters of ethanol and 1.0 liter of water having a polarity of 53.7 kcal/mol. 1.04 kg of saccharin were added to this solution. Subsequently, this reaction mixture was cooled to a temperature of 8° C. and stirred at this temperature for a further 16 hours. This resulted in the formation of a crystalline precipitate of (1RS,2RS)-2-[(dimethylamino)methyl]-1-(3-methoxyphenyl)cyclohexanol saccharinate which was removed from the mother liquor by suction filtration under reduced pressure using a G3 frit. The crystalline precipitate was twice washed with 2.0 liters of ethanol each time which had been cooled beforehand to a temperature of 8° C., and then dried in a vacuum drying cabinet at a temperature of 40° C. and a pressure of 20 mbar for 16 hours. The yield of the product obtained in this way was 1.53 kg (corresponding to 60% of the theoretically calculated value) having a content of (1RS,2RS)-2-[(dimethylamino)methyl]-1-(3-methoxyphenyl)cyclohexanol saccharinate of >99% by weight.

Example 4

In a 10 liter jacketed reaction apparatus equipped with electric anchor stirrer, reflux condenser, thermometer and cooling/heating unit (from Huber, Unistat 161 W), 1.5 kg of the mixture obtained by the above-specified Grignard reaction were dissolved at a temperature of 20° C. in 5.0 liters of water having a polarity of 63.1 kcal/mol. 1.04 kg of saccharin were added to this solution. Subsequently, this reaction mixture was cooled to a temperature of 8° C. and stirred at this temperature for a further 16 hours. This resulted in the formation of a crystalline precipitate of (1RS,2RS)-2-[(dimethylamino)methyl]-1-(3-methoxyphenyl)cyclohexanol saccharinate which was removed from the mother liquor by suction filtration under reduced pressure using a G3 frit. The crystalline precipitate was twice washed with 2.0 liters of ethanol each time which had been cooled beforehand to a temperature of 8° C., and then dried in a vacuum drying cabinet at a temperature of 40° C. and a pressure of 20 mbar for 16 hours. The yield of the product obtained in this way was 2.16 kg (corresponding to 85% of the theoretically calculated value) having a content of (1RS,2RS)-2-[(dimethylamino)methyl]-1-(3-methoxyphenyl)cyclohexanol saccharinate of >90% by weight.

Example 5

In a 20 liter jacketed reaction apparatus equipped with electric anchor stirrer, reflux condenser, thermometer and cooling/heating unit (from Huber, Unistat 161 W), 1.0 kg of the mixture obtained by the above-specified Grignard reaction were dissolved at a temperature of 20° C. in 14 liters of acetone having a polarity of 42.2 kcal/mol. 0.69 kg of saccharin was added to this solution. Subsequently, this reaction mixture was cooled to a temperature of 8° C. and stirred at this temperature for a further 16 hours. This resulted in the formation of a crystalline precipitate of (1RS,2RS)-2-[(dimethylamino)methyl]-1-(3-methoxyphenyl)cyclohexanol saccharinate which was removed from the mother liquor by suction filtration under reduced pressure using a G3 frit. The crystalline precipitate was twice washed with 3 liters of acetone each time which had been cooled beforehand to a temperature of 8° C., and then dried in a vacuum drying cabinet at a temperature of 40° C. and a pressure of 20 mbar for 16 hours. The yield of the product obtained in this way was 1.09 kg (corresponding to 64% of the theoretically calculated value) having a content of (1RS,2RS)-2-[(dimethylamino)methyl]-1-(3-methoxyphenyl)cyclohexanol saccharinate of >96% by weight.

What is claimed is:

1. A process for isolating and purifying (1RS,2RS)-2-[(dimethylamino)methyl]-1-(3-methoxyphenyl)cyclohexanol as the saccharinate from a mixture consisting of the diastereomers (1RS,2RS)-2-[(dimethylamino)methyl]-1-(3-methoxyphenyl)-cyclohexanol and (1SR,2RS)-2-[(dimethylamino)methyl]-1-(3-methoxyphenyl)cyclohexanol and also in some cases impurities, characterized in that the mixture is reacted with saccharin in a reaction medium which is liquid at 20° C. and atmospheric pressure and has a polarity of at least 38 kcal/mol, and removing the thus-obtained crystalline precipitate of the saccharinate of (1RS,2RS)-2-[(dimethylamino)methyl]-1-(3-methoxy-phenyl)cyclohexanol diastereomers from the mother liquor.

2. The process of claim 1, characterized in that the crystalline precipitate is washed at least once and/or recrystallized and subsequently dried at least once.

3. The process of claim 1 characterized in that the polarity of the reaction medium is at least 45 kcal/mol.

4. The process of claim 1, characterized in that the mixture comprises at least 50% by weight of the (1RS,2RS)-2-[(dimethyl amino)methyl]-1-(3-methoxy-phenyl) cyclohexanol diastereomer.

5. The process of claim 1, characterized in that the reaction medium used is water, an aliphatic alcohol, an aliphatic ketone, an aliphatic ester, an aliphatic and/or aromatic ester, an aliphatic and/or aromatic ether, a polyol, a haloalkane, an aliphatic or aromatic nitrile or a mixture of at least two of these aforementioned compounds.

6. The process of claim 5, characterized in that the reaction medium used is water, a $C_{1-6}$-alcohol, an aliphatic $C_{3-7}$-ketone, an aliphatic $C_{2-6}$-ester, an aliphatic and/or aromatic $C_{7-12}$-ester, an aliphatic $C_{4-6}$-ether, a $C_{1-2}$-haloalkane, an aliphatic or aromatic nitrile, a $C_{2-10}$-polyol or a mixture of at least two of these aforementioned compounds.

7. The process of claim 6, characterized in that the reaction medium used is water, methanol, ethanol, n-propanol, isopropanol, n-butanol, isobutanol, ethyl acetate, n-butyl acetate, methyl formate, methyl ethyl ketone, diisopropyl ether, anisole, ethylene glycol, propylene glycol, acetone or a mixture of at least two of these aforementioned compounds.

8. The process of claim 7, characterized in that the reaction medium used is a mixture of water and ethanol or of water and acetone.

9. The process of claim 5, characterized in that the mixture is of from 60 to 95% by weight of an organic compound and from 5 to 40% by weight of water based on the entire amount of the reaction medium.

10. The process of claim 1, characterized in that the mixture is cooled during and/or immediately after the reaction with saccharin.

11. The process of claim 10, characterized in that the mixture is cooled to a temperature of from 2 to 15° C.

12. The process of claim 1, characterized in that the mixture is stirred before the crystalline precipitate is removed.

13. The process of claim 12, characterized in that the mixture is stirred for from 5 to 25 hours.

14. The process of claim 1, characterized in that the precipitate is removed from the mother liquor by centrifugation, suction filtration, decanting or a combination of these methods.

15. The process of claim 2, characterized in that the reaction medium is used to wash the precipitate.

16. The process of claim 15, characterized in that the reaction medium is cooled.

17. The process of claim 16, characterized in that the reaction medium is cooled to a temperature of from 2 to 15° C.

18. The process of claim 1, characterized in that the impurities are by-products which stem from the Grignard reaction for preparing the diastereomer mixture of (1RS, 2RS)-2-[(dimethylamino)methyl]-1-(3-methoxyphenyl) cyclo-hexanol and (1SR,2RS)-2-[(dimethylamino)methyl]-1-(3-methoxyphenyl) cyclohexanol.

19. The process of claim 1, characterized in that the (1RS,2RS)-2-[(dimethyl-amino)methyl]-1-(3-methoxyphenyl)cyclohexanol saccharinate is released with at least one base in a solvent or solvent mixture and the thus-obtained free (1RS,2RS)-2-[(dimethylamino)methyl]-1-(3-methoxyphenyl)cyclohexanol base is purified and isolated.

20. The process of claim 19, characterized in that the base is used in an equimolar amount or in excess, based on the (1RS,2Rs}-2-[(dimethylamino}methyl]-1-(3-methoxyphenyl)cyclohexanol saccharinate.

21. The process of claim 19, characterized in that the (1RS,2RS)-2-[(dimethyl-amino) methyl]-1-(3-methoxyphenyl)cyclohexanol is converted to the corresponding active ingredient salt by reacting with an acid.

22. The process of claim 1 where the polarity of the reaction medium is at least 55 kcal/mol.

23. The process of claim 1, where the mixture comprises at least 60% by weight, of the (1RS,2RS)-2-[(dimethyl amino)methyl]-1-(3-methoxy-phenyl) cyclohexanol diastereomer.

24. The process of claim 5, where the mixture is of from 70 to 90% by weight of an organic compound and from 10 to 30% by weight of water based in each case on the entire amount of the reaction medium.

25. The process of claim 5, where the mixture is of from 75 to 85% by weight of an organic compound and from 15 to 25% by weight of water based in each case on the entire amount of the reaction medium.

26. The process of claim 10, characterized in that the mixture is cooled to a temperature of from 5 to 10° C.

27. The process of claim 12, characterized in that the mixture is stirred for from 10 to 20 hours.

28. The process of claim 16, characterized in that the reaction medium as cooled to a temperature of from 5 to 100 C.

* * * * *